United States Patent [19]
Green et al.

[11] Patent Number: 5,449,365
[45] Date of Patent: Sep. 12, 1995

[54] SURGICAL CLAMP APPARATUS

[75] Inventors: David T. Green, Westport, Conn.;
Boris Zvenyatsky, Bronx, N.Y.

[73] Assignee: United States Surgical Corporation, Norwalk, Conn.

[21] Appl. No.: 229,867

[22] Filed: Apr. 19, 1994

Related U.S. Application Data

[63] Continuation of Ser. No. 939,137, Sep. 2, 1992, abandoned.

[51] Int. Cl.$^6$ .............................................. A61B 17/00
[52] U.S. Cl. ..................... 606/142; 606/139; 606/151; 227/901
[58] Field of Search ............... 606/142, 143, 147, 151, 606/157, 158, 139, 205, 206–208; 227/901, 902; 128/831, 843

[56] References Cited

U.S. PATENT DOCUMENTS

| | | |
|---|---|---|
| 3,279,479 | 10/1966 | Solomon . |
| 3,378,010 | 4/1968 | Codling et al. . |
| 3,506,012 | 4/1970 | Brown . |
| 3,802,437 | 4/1974 | Kees, Jr. ............... 606/158 |
| 3,874,042 | 4/1975 | Eddleman et al. . |
| 3,882,854 | 5/1975 | Hulka et al. . |
| 3,916,908 | 11/1975 | Leveen . |
| 3,926,195 | 12/1975 | Bleier et al. ............... 128/831 |
| 3,954,108 | 5/1976 | Davis . |
| 3,958,576 | 5/1976 | Komiya . |
| 4,038,987 | 8/1977 | Komiya . |
| 4,064,881 | 12/1977 | Meredith . |
| 4,169,476 | 10/1979 | Hiltebrandt . |
| 4,192,315 | 3/1980 | Hilzinger et al. . |
| 4,273,129 | 6/1981 | Boebel . |
| 4,274,415 | 6/1981 | Kanamoto et al. ............... 606/158 |
| 4,325,377 | 4/1982 | Boebel . |
| 4,367,746 | 1/1983 | Derechinsky . |
| 4,440,170 | 4/1984 | Golden et al. . |
| 4,602,631 | 7/1986 | Funatsu ............... 606/142 |
| 4,635,634 | 1/1987 | Santos . |
| 4,651,737 | 3/1987 | Deniega . |
| 4,674,501 | 6/1987 | Greenberg ............... 606/142 |
| 4,706,668 | 11/1987 | Backer . |
| 4,796,625 | 1/1989 | Kees, Jr. . |
| 4,817,604 | 4/1989 | Smith, III . |
| 4,872,456 | 10/1989 | Hasson ............... 606/207 |
| 4,919,152 | 4/1990 | Ger . |
| 4,929,240 | 5/1990 | Kirsch et al. . |
| 4,931,058 | 6/1990 | Cooper . |
| 4,935,026 | 6/1990 | McFadden . |
| 4,943,298 | 7/1990 | Fujita et al. . |
| 4,944,741 | 7/1990 | Hasson ............... 606/207 |
| 4,950,273 | 8/1990 | Briggs . |
| 4,957,500 | 9/1990 | Liang et al. . |
| 4,983,176 | 1/1991 | Cushman et al. . |
| 5,026,379 | 6/1991 | Yoon . |
| 5,049,153 | 9/1991 | Nakao et al. . |
| 5,053,045 | 10/1991 | Schmidt et al. . |
| 5,059,202 | 10/1991 | Liang et al. . |
| 5,074,870 | 12/1991 | von Zeppelin . |
| 5,078,731 | 1/1992 | Hayhurst . |
| 5,084,057 | 1/1992 | Green et al. . |
| 5,100,418 | 3/1992 | Yoon et al. . |
| 5,100,420 | 3/1992 | Green et al. . |
| 5,125,553 | 6/1992 | Oddsen et al. . |
| 5,147,373 | 9/1992 | Ferzli ............... 606/207 |
| 5,163,945 | 11/1992 | Ortiz et al. . |
| 5,176,702 | 1/1993 | Bales et al. ............... 606/208 |
| 5,234,443 | 8/1993 | Phan et al. ............... 606/148 |
| 5,242,456 | 9/1993 | Nash et al. ............... 606/142 |
| 5,258,007 | 11/1993 | Spetzler et al. ............... 606/142 |
| 5,282,806 | 2/1994 | Haber et al. ............... 606/148 |

Primary Examiner—Stephen C. Pellegrino
Assistant Examiner—Jeffrey A. Schmidt

[57] ABSTRACT

Apparatus is provided for applying a surgical clamp during endoscopic or laparoscopic procedures which includes a handle portion, an endoscopic portion extending longitudinally from the handle portion, and a surgical clamp detachably mounted adjacent a distal end of the endoscopic portion. The surgical clamp includes opposed cooperating jaw members which are movable between an initially closed position and an open position. Structure is associated with the endoscopic portion of the apparatus for detachably engaging the surgical clamp and a mechanism is provided for moving the opposed cooperating jaws between the initially closed position and the open position and for moving the engaging structure between a disengaged position and an engaged position. Preferably, a distal end portion of the endoscopic portion of the apparatus is adapted to articulate relative the longitudinal axis of the endoscopic portion for increasing the range of operability of the apparatus during surgical procedures.

32 Claims, 10 Drawing Sheets

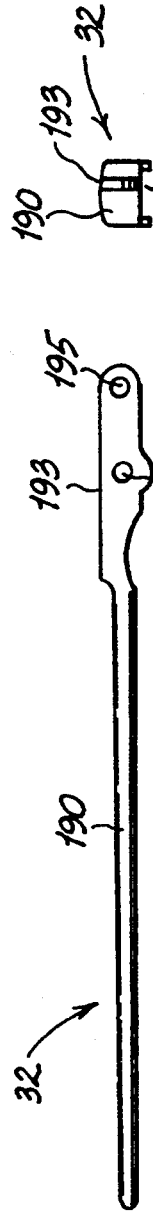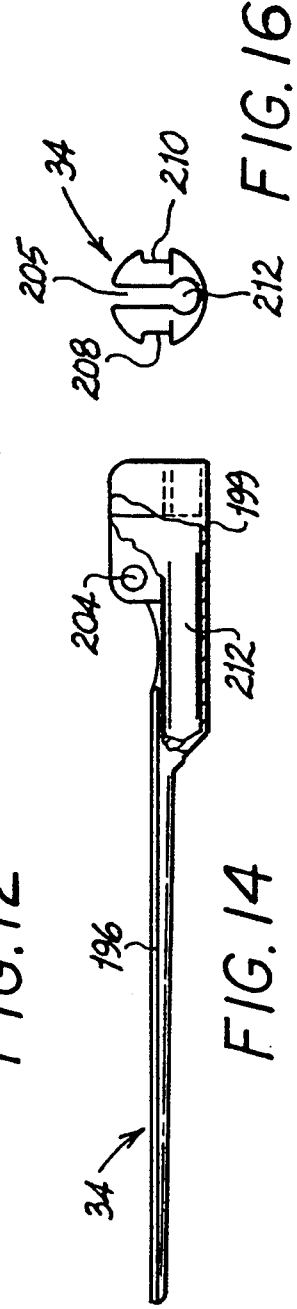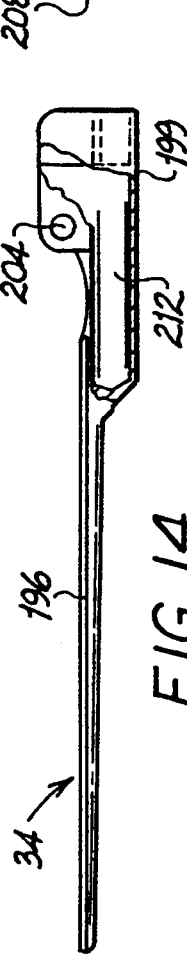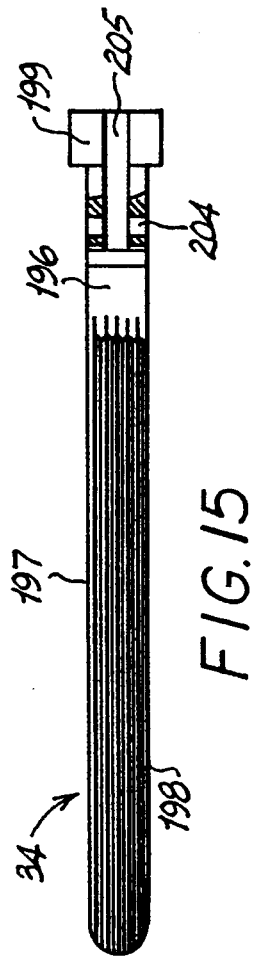

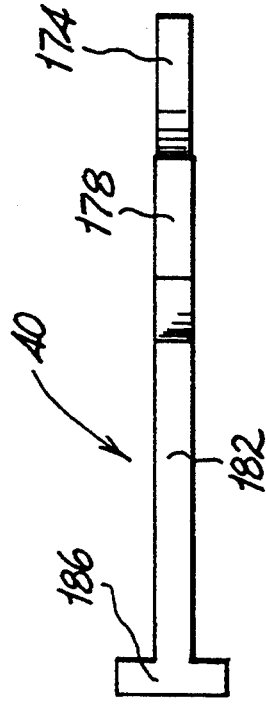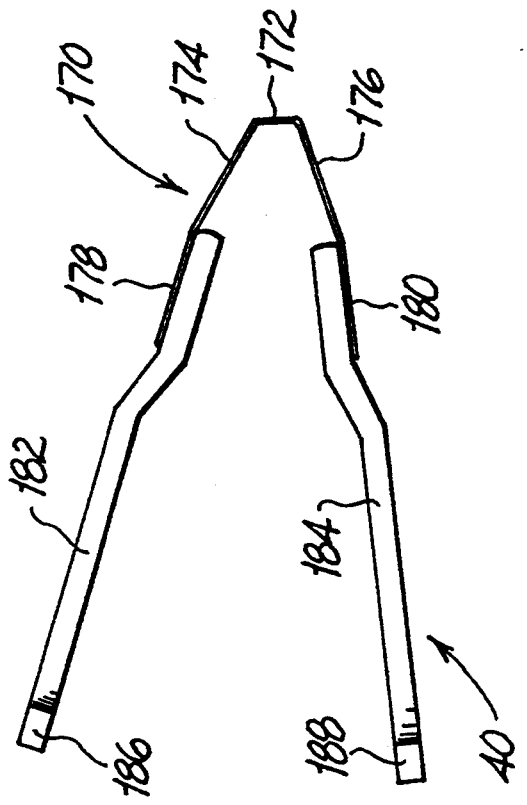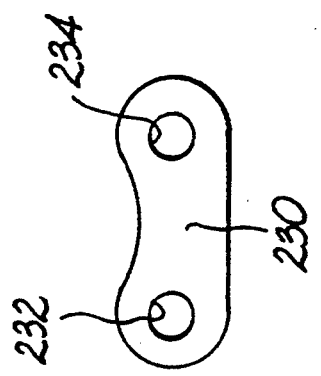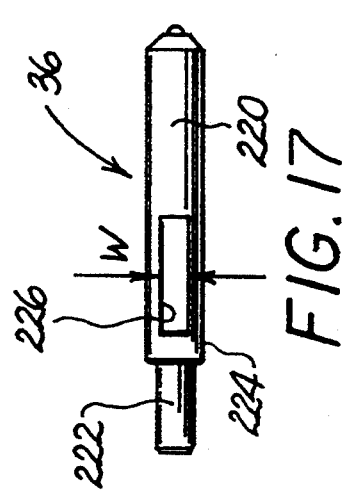

SURGICAL CLAMP APPARATUS

This is a continuation of application Ser. No. 07/939,137, filed on Sep. 2, 1992, now abandoned.

BACKGROUND OF THE INVENTION

1. Field of the Invention

The subject invention relates to surgical apparatus for performing laparoscopic and endoscopic surgical procedures, and more particularly to a surgical clamp apparatus and method for applying the clamp during a surgical procedure.

2. Description of Related Art

During surgical operations in which it is necessary to open the intestinal wall to expose the interior lumen, a surgeon must place a clamp across the intestine above and below the point of entry. Prior art surgical clamping devices for clamping tubular vessels such as the intestines are well known. For example, U.S. Pat. No. 4,976,721 to Blasnik et al. describes a manually operable clamp having parallel jaw members biased in a closed position by a spring which is maintained within a housing portion of the clamp. Other surgical clamps having spring biased parallel jaw members include those described in U.S. Pat. No. 3,509,882 to Blake and U.S. Pat. No. 4,931,058 to Cooper.

A bowel clamp and a detachable applicator for applying the clamp are disclosed in U.S. Pat. No. 3,916,908 to Leveen. In particular, Leveen shows a disposable bowel clamp which comprises two rod members each having a hook structure at one end thereof and an aperture at the opposed end which the hook structure engages. Each of the rods are held within respective jaws of the applicator in such a manner so that the jaws of the applicator, once closed, fasten the rod members securely together, thereby forming a clamp. Once the clamp has been placed on the vessel, the applicator is detached from the clamp and removed for use elsewhere. The apparatus shown in Leveen is limited in application however, to conventional surgical procedures in which the surgeon has direct access to the abdominal cavity.

There is a perceived need in the art for adaptation of a detachable bowel clamp, such as that disclosed in Leveen, for endoscopic or laparoscopic procedures. In these procedures a small incision or puncture is made in the patient's body to provide access for a tube or cannula device which allows insertion of surgical apparatus. Thus, to avoid requiting separate incisions for each instrument having a clamp, there is a perceived need in the art for a clamp detachably mounted to the instrument which could be inserted through a cannula, clamped onto a vessel and which remains there while the instrument which delivered the clamp to the site is withdrawn through the cannula and used to deliver another clamp to the operative site.

Such an endoscopic surgical instrument having a detachable clamp for the bowel would, like other bowel clamps, have atraumatic jaws which are angled and include tabs for preventing the bowel from slipping out. The handle and the jaws of the instrument would also be spring loaded, and as is desirable with endoscopic instruments, the instrument would be rotatable and capable of angling for easier application of the clamp.

While there is a perceived need in the art for the above-described instrument, due to the complexity of such an instrument, to date no one has developed an endoscopic instrument which enables the application and withdrawal of detachable bowel clamps. The complexity of such an instrument, and hence the difficulty of its development, is due to the requirements that it be operable at a region remote from the clamp to actuate the jaws of the clamp, detach the clamp, re-attach the clamp at the surgical site, as well as allow for rotation and angling of the instrument.

SUMMARY OF THE INVENTION

While the subject invention is described herein with respect to a device for applying a bowel clamp, the applicability of the instrument should not be limited thereto for it is envisioned that the surgical apparatus of the subject invention would be useful in many endoscopic or laparoscopic procedures wherein it is necessary to apply a surgical clamp to a tubular vessel.

A surgical apparatus is therefore disclosed, in accordance with a preferred embodiment of the subject invention, for applying a surgical clamp during an endoscopic procedure and subsequently retrieving the clamp upon completion of the procedure. The apparatus comprises a handle portion, an endoscopic portion which extends longitudinally from the handle portion, and a surgical clamp which is detachably mounted adjacent a distal end of the endoscopic portion of the instrument. The clamp includes a pair of opposed cooperating jaw members which are movable between a normally closed position and an open position. The apparatus further comprises structural means, associated with the endoscopic portion of the instrument, for detachably engaging the clamp which comprises a pair of opposed engaging arms mounted on a resilient base structure and adapted to be cammed from an outstretched disengaged position to an engaged position wherein the engaging arms interlock with the surgical clamp. The instrument is also provided with means for moving the opposed cooperating jaw members of the surgical clamp between the normally closed position and the open position.

Preferably, a distal end portion of the endoscopic portion of the apparatus is adapted for articulation relative to the longitudinal axis of the endoscopic portion so as to increase the range of operability of the instrument. Accordingly, the apparatus includes means which are associated with the handle portion thereof for effectuating the articulation of the distal end portion of the endoscopic portion. The apparatus also includes seal means which are provided in the endoscopic portion thereof for inhibiting the egress of insufflation gas therethrough.

The subject invention is further directed to a method for applying a surgical clamp during an endoscopic or laparoscopic procedure which includes the steps of providing an apparatus including a handle portion and an endoscopic portion extending from the handle portion having opposed engaging arms at a distal end thereof for detachably mounting a surgical clamp, engaging the surgical clamp adjacent the distal end portion of the endoscopic portion of the apparatus, extending the endoscopic portion and the clamp through a cannula device and into the abdominal cavity of the patient, moving the opposed jaw members from an initially closed position to an open position, positioning the clamp in a desired position relative to the tubular vessel to be clamped, moving the opposed jaw member of the clamp from the open position to a closed position, and disengaging the opposed engaging arms from the surgical clamp so as to detach the clamp from the distal end portion of the apparatus.

Further features of the subject invention will become more readily apparent from the following detailed description of the invention taken in conjunction with the accompanying drawings.

BRIEF DESCRIPTION OF THE DRAWINGS

Preferred embodiments of the subject invention will be described hereinbelow with reference to the drawings, wherein:

FIG. 11 is a side elevational view of the upper jaw member of the surgical clamp of the subject invention;

FIG. 12 is a rear elevational view of the upper jaw member of FIG. 11;

FIG. 13 is a bottom plan view of the upper jaw member of FIG. 11;

FIG. 14 is a side elevational view, partially broken away, of the lower jaw member of the surgical clamp of the subject invention;

FIG. 15 is a rear elevation view of the lower jaw member of FIG. 14;

FIG. 16 is a top plan view, in partial cross-section, of the lower jaw member of FIG. 14;

FIG. 17 is a top plan view of the barrel member shown in FIG. 3;

FIG. 18 is a side elevational view of the link member shown in FIG. 3;

FIG. 19 is a side elevational view of the surgical clamp engaging structure shown in FIG. 3; and FIG. 20 is a top plan view of the surgical clamp engaging structure of FIG. 19.

DETAILED DESCRIPTION OF THE PREFERRED EMBODIMENTS

Figure 1:
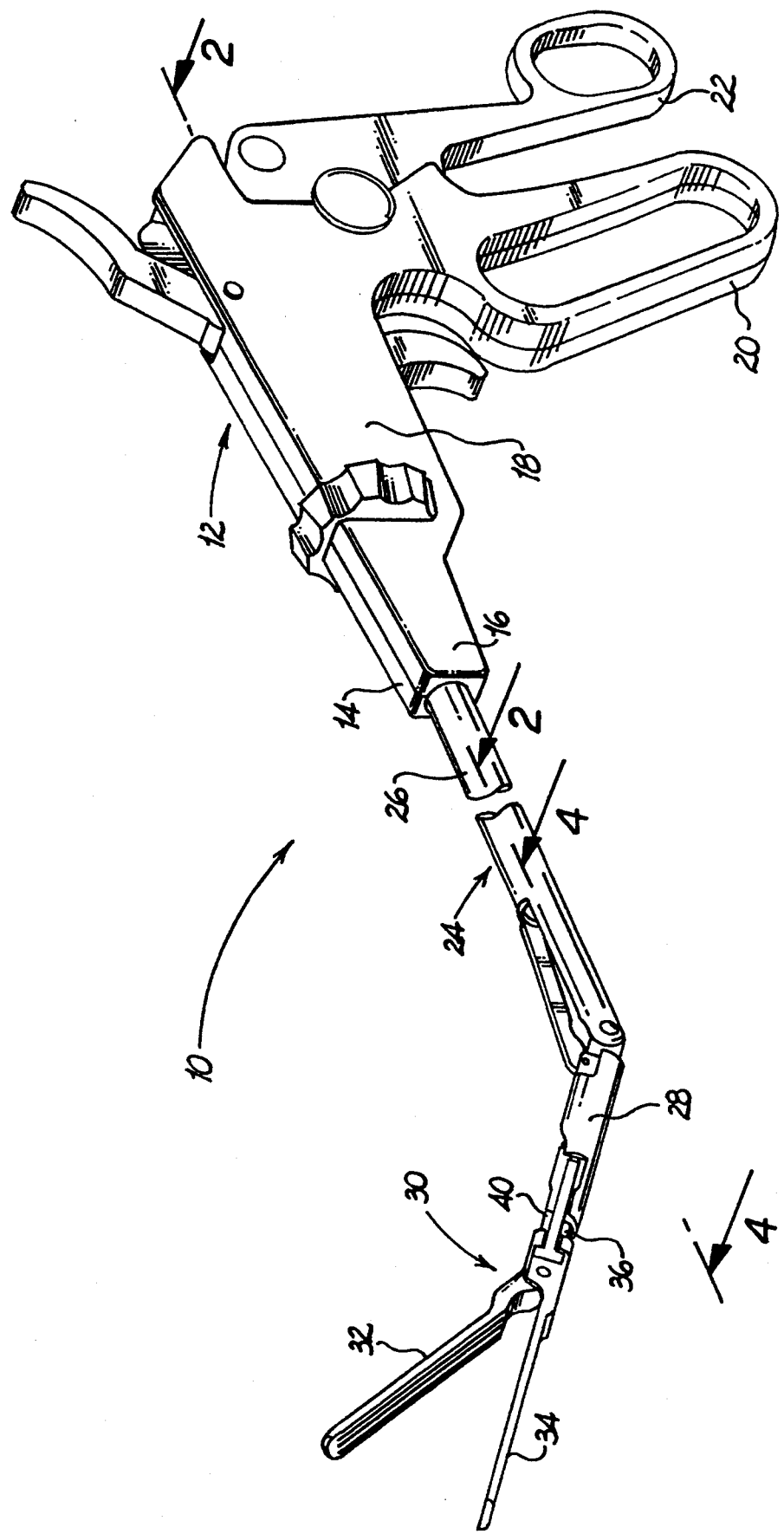
FIG. 1 is a perspective view of an endoscopic surgical apparatus in accordance with a preferred embodiment of the subject invention.

In the drawings and in the description which follows, the term "proximal" refers to the end which is closest to the operator while the term "distal" will refer to the end which is furthest from the operator.

The surgical apparatus of the subject invention is illustrated in FIG. 1 and is designated generally by reference numeral 10. Surgical apparatus 10 comprises a handle portion 12 including opposed hemi-portions 14 and 16 which are mounted to one another to define a body 18 and a fixed handle 20. A pivoting handle 22 is movably connected to body 18 adjacent fixed handle 20. Surgical apparatus 10 further comprises an endoscopic portion 24 which extends from the body 18 of handle portion 12 and which includes an elongated proximal portion 26 and an articulating portion 28 which is movably mounted at a distal end of proximal portion 26. A surgical clamp 30 having opposed cooperating jaw members 32 and 34 is detachably mounted to the articulating portion 28 of endoscopic portion 24 by a barrel 36 which extends outwardly from surgical clamp 30. Engaging structure 40 is associated with the articulating portion 28 for detachably mounting surgical clamp 30 to apparatus 10.

Figure 2:
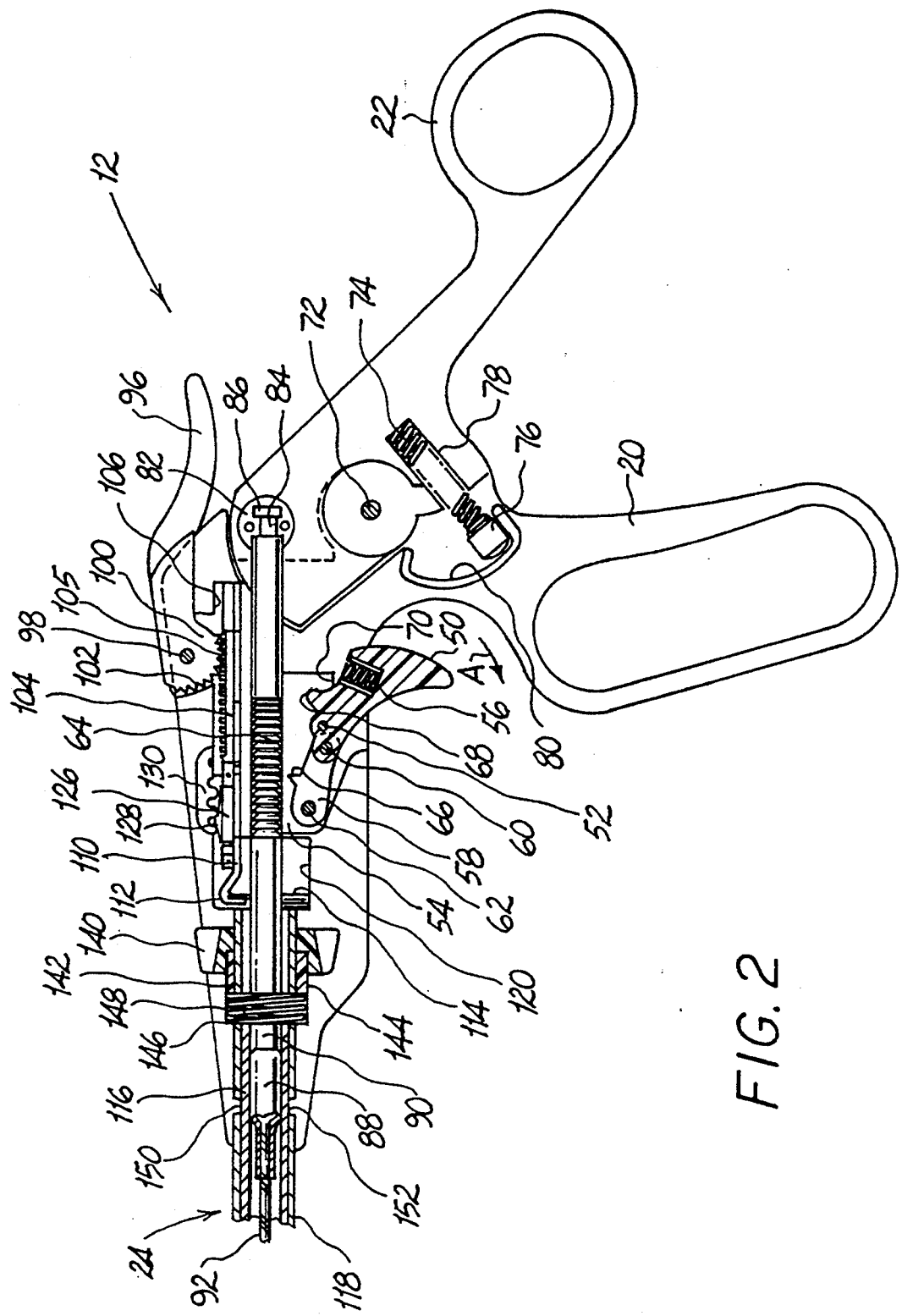
FIG. 2 is an enlarged side elevational view in cross-section taken along line 2—2 of FIG. 1.

Referring to FIG. 2, handle portion 12 further comprises a trigger mechanism which includes a trigger 50 pivotably mounted to body portion 18 by a pin 52 and movable within a chamber 54 which is defined in body portion 18. Trigger 50 is provided with an internal spring member 56 which biases trigger 50 into an engaging position in the direction of indicator arrow "A". Once biased into the engaging position, a ratchet link 58, which is pivotably connected to trigger 50 by a pin 60 and which is mounted within trigger chamber 54 by a pin 62, engages a rack member 64 mounted for reciprocating longitudinal movement in body portion 18 and operatively associated with the endoscopic portion 24 of surgical apparatus 10. Specifically, a ratchet catch 66 which depends from ratchet link 58 is engagable between a plurality of teeth defined in rack member 64 for selectively controlling the longitudinal movement of rack member 64. In addition, a travel stop detent 68 extends rearwardly from trigger 50 for stopping trigger 50 against a shelf 70 which is formed in chamber 54 as biasing spring 56 returns trigger 50 to its engaging position.

Pivoting handle 22 is mounted to the body 18 of handle portion 12 by a pivot pin 72. A biasing spring 74 and a thrust member 76 are mounted within a slot 78 in pivoting handle 22 and extend into a groove 80 formed in fixed handle 20. Compression of pivoting handle 22 in the direction of indicator arrow "B" will compress biasing spring 74 against thrust member 76 so as to store energy to return the pivoting handle 22 when it is released. A universal joint member 82 is associated with the upper portion of pivoting handle 22 and is operatively connected to a mechanism for controlling the cooperative movement of the jaws 32 and 34 of surgical clamp 30, and in addition, for controlling the engaging structure 40 which is associated with the articulating portion 28 of endoscopic portion 24 for detachably engaging surgical clamp 30. The control mechanism includes an elongated rod member 84 having a head 86 formed at the proximal end thereof which is engaged in a universal joint 82. The distal end of rod member 84 is engaged in a coupling member 88 which is disposed in endoscopic portion 24 and more particularly, within an inner tube 90 of endoscopic portion 24. A proximal end of an elongated control cable 92 is engaged in coupling member 88 and a distal end of control cable 92 extends operatively through endoscopic portion 24 to engaging structure 40.

Handle portion 12 further comprises a mechanism for moving the articulating portion 28 of endoscopic portion 24 relative to the longitudinal axis of proximal portion 26. The articulating mechanism includes a latch member 96 which is pivotably mounted in the body 18 of handle portion 12 by a pivot pin 98. Latch member 96 is formed with an arcuate portion 100 having a plurality of gear teeth 102 defined thereon. Gear teeth 102 mesh operatively with an elongated rack member 104 having corresponding gear teeth 105 and disposed movably within a longitudinal chamber 106 formed in handle portion 12. A draw arm 110 is mounted to the undersurface of rack member 104 and includes a hook structure 112 formed at a distal end thereof. Hook structure 112 is adapted and configured to engage a flange-like structure 114 formed on the proximal end of an internal tube 116 which is operatively mounted for coaxial translation within an outer tube 118 of endoscopic portion 24. Flange-like structure 114 is dimensioned to translate within an annular chamber 120 defined in the body 18 of handle portion 12. Manipulation of latch member 96 will cause gear teeth 102 on the annular portion 100 of latch member 96 to operatively intermesh with teeth 105 on rack member 104, moving it in a longitudinal direction within chamber 106, so as to cause draw arm 110 to move the internal tube 116 longitudinally.

An adjustable leaf spring 126 is operatively associated with draw arm 110 and has an engaging detent 128 formed thereon which is engagable within a grooved section 130 of the body 18 of handle portion 12. Grooved section 130 has a plurality of a grooved receptacle areas for receiving detent 128 which correspond to a plurality of angular positions of articulating portion 28. More particularly, the receptacle areas correspond to a first position of articulation equal to 0°, a second position of articulation equal to 30°, a third position of articulation equal to 60°, and a fourth position equal to 90° of articulation. Movement of the articulating portion 28 of endoscopic portion 24 is achieved by translating the longitudinal movement of internal tube member 116 to an elongated link member 132 which is pivotably mounted at a proximal end 134 thereof to a joint member 135 on the end of internal tube member 116 and at a distal end 136 thereof to articulating portion 28 (see FIGS. 3 and 4). Proximal movement of internal tube member 116 in response to rotation of latch member 96 will cause link member 132 to urge articulating portion 28 into an articulated position relative to the longitudinal axis of the proximal portion 26 of endoscopic portion 24. Clearly, the instrument can be configured to allow articulation to other angular position than those which are discussed above.

Referring again to FIG. 2, handle portion 12 further comprises a mechanism for rotating endoscopic portion 24 about the longitudinal axis thereof relative to handle portion 12. The rotation mechanism includes a rotator member 140 mounted within body portion 18 and having a central passageway extending therethrough for accommodating the tubular structures of endoscopic portion 24. A thrust collar 142 is engaged in an annual recess 144 defined in rotator member 140 and is maintained therein by a biasing spring 146 which is disposed in a chamber 148 defined adjacent the distal end of body portion 18. Opposed detents 150 and 152 are also associated with the distal end portion of body 18 for interlocking with corresponding apertures in outer tube 118 of endoscopic portion 24 so as to rigidly mount endoscopic portion 24 to handle portion 12.

Endoscopic portion 24 is further provided with a plurality of seal members which are positioned to inhibit the egress of insufflation gas from the operative site through endoscopic portion 24. A first seal member 151 is preferably disposed in the distal end of proximal portion 26 adjacent articulating portion 28 and a second seal member 153 is preferably disposed in proximal portion 26 adjacent handle portion 12.

Figure 3:
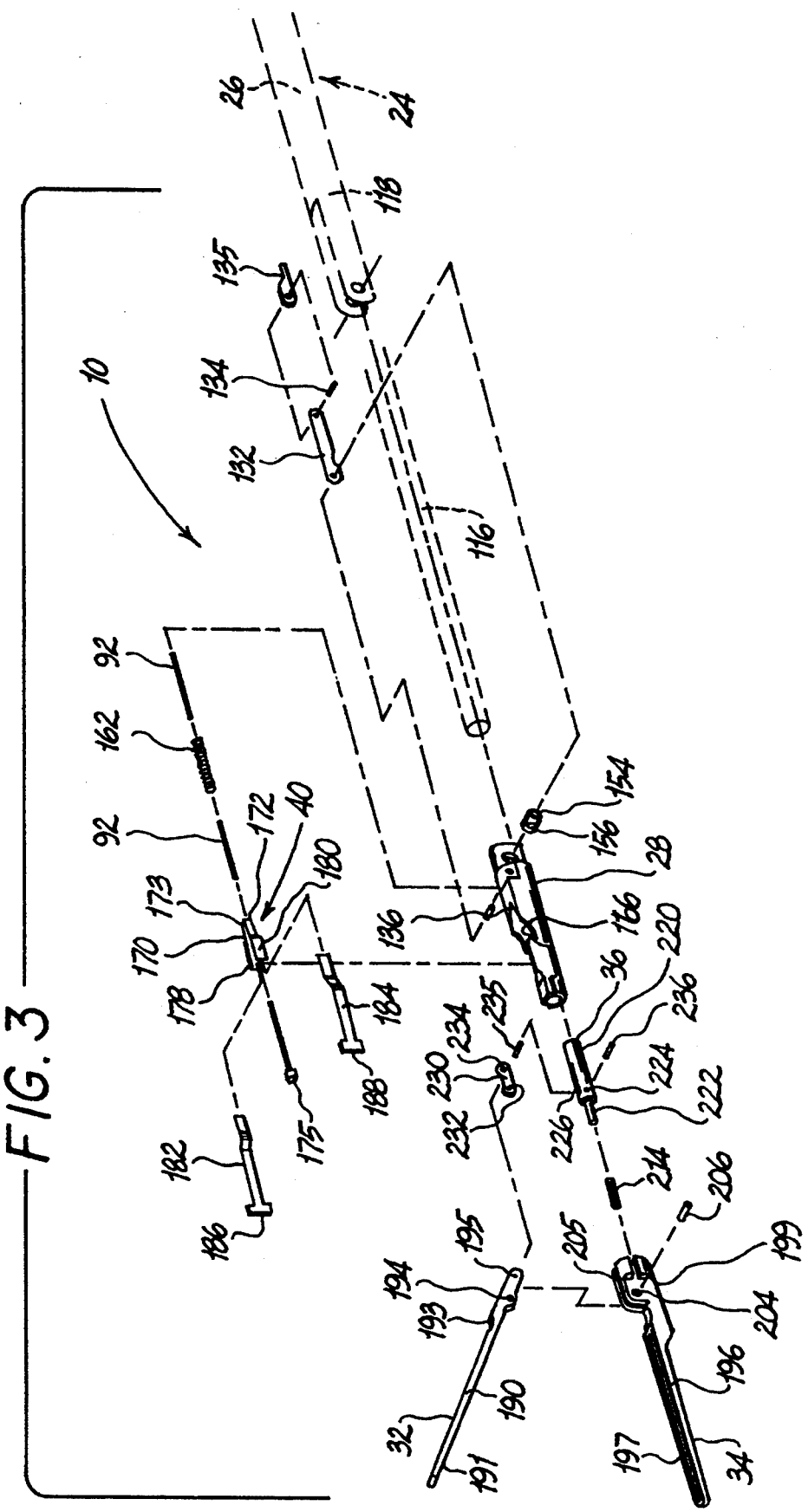
FIG. 3 is an exploded perspective view of the distal end portion of the endoscopic surgical apparatus of FIG. 1.
Figure 4:
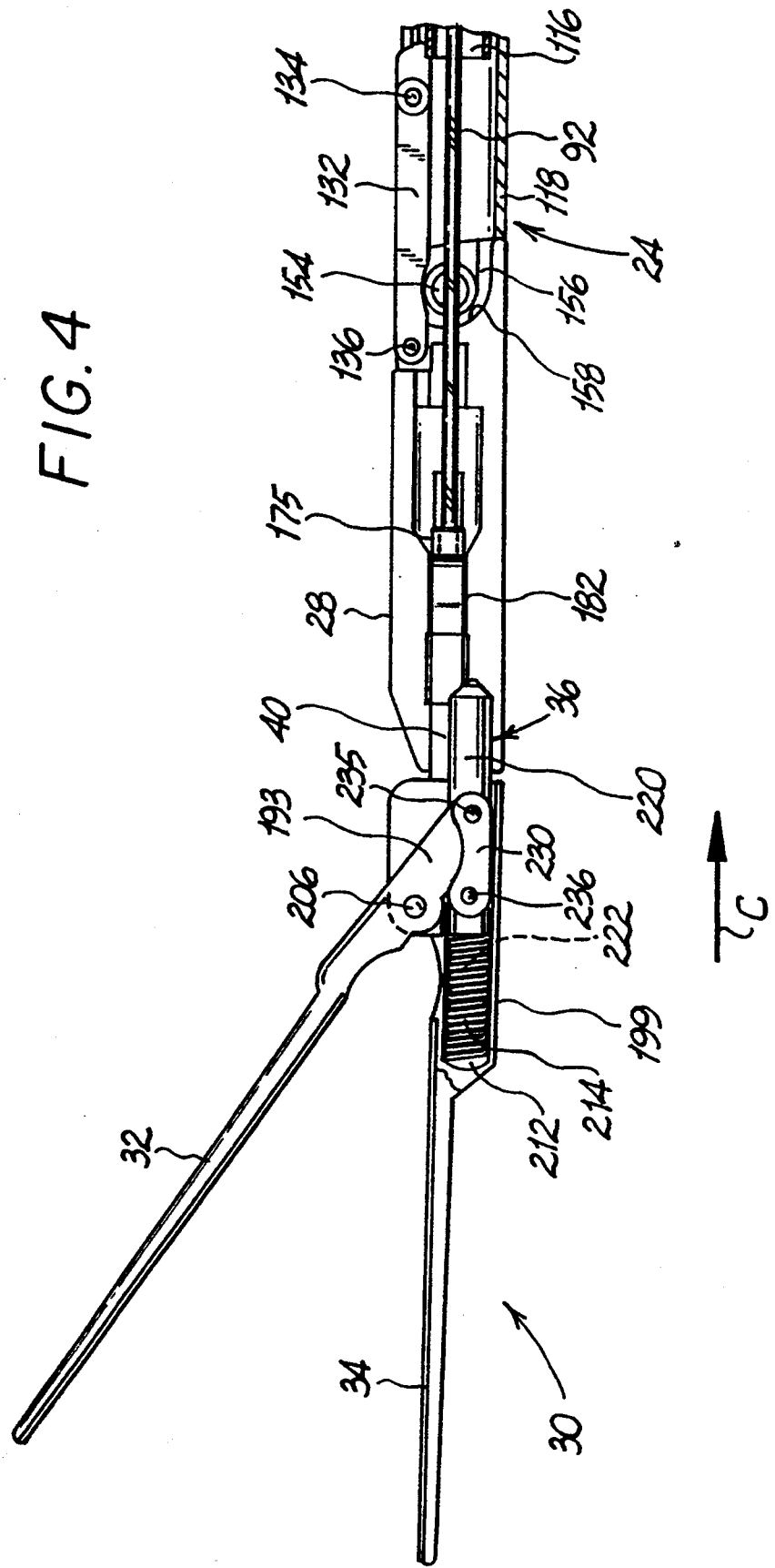
FIG. 4 is an enlarged side elevational view of the surgical apparatus of FIG. 1.
Figure 5:
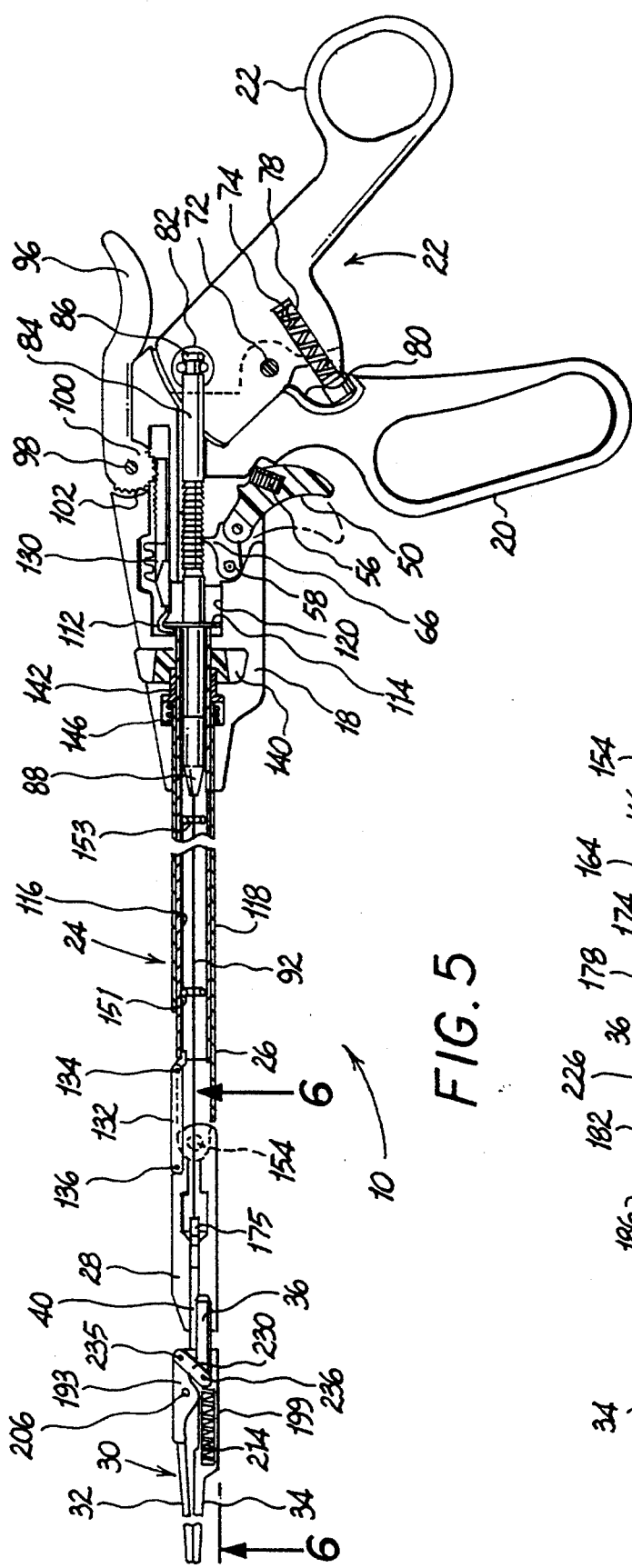
FIG. 5 is a side elevational view in cross-section of the apparatus of FIG. 1 with the surgical clamp in a normally closed position.
Figure 6:
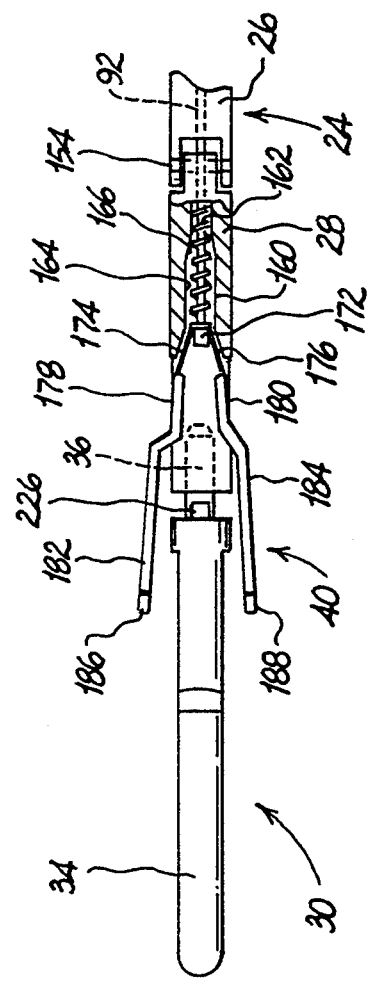
FIG. 6 is a top plan view in cross-section taken along line 6—6 of FIG. 5 with the engaging structure in a disengaged position.

Referring to FIGS. 3, 4 and 6, the articulating portion 28 of endoscopic portion 24 is movably mounted adjacent the distal end of elongated proximal portion 26 by a transverse pin pivot 154. A longitudinal bore 156 having a diverging inlet port 158 extends through pin pivot 154 for accommodating the passage of control cable 92. Diverging inlet port 158 functions to limit any undue bending of cable 92 which may be caused when the articulating portion 28 is pivoted about pivot pin 154. A passageway 160 extends longitudinally through articulating portion 28 for accommodating a plurality of components including a spring member 162 (see FIG. 6) which serves to bias the engaging structure 40 in a distal direction. In particular, spring member 162 is disposed in a substantially cylindrical intermediate chamber 164 of passageway 160, the walls of which diverge to define a generally V-shaped distal chamber 166 for accommodating a structural portion of engaging structure 40.

Referring to FIGS. 3-7, 19 and 20, engaging structure 40 is movable from a disengaged position (FIGS. 6 and 20) to an engaged position by operation of pivoting handle 22 in handle portion 12 for detachably mounting surgical clamp 30 to the articulating portion 28 of endoscopic portion 24. Engaging structure 40 includes a structural portion 170 having a base 172 from which extends a pair of opposed resilient legs 174 and 176 defining camming surfaces and each having a mounting portion 178 and 180 formed thereon respectively. Lateral engaging arm members 182 and 184 having T-shaped head portions 186 and 188, respectively, extend from mounting portions 178 and 180 of structural portion 170. In a disengaged position, engaging structure 40 extends partially into the V-shaped chamber 166 of passageway 160 so that spring member 162 is biased against the base 172 of structural portion 170 and the opposed resilient legs 174 and 176 extend radially outwardly from the base 172. Control cable 92 extends through an aperture 173 in the base 172 of structural portion 170 and is maintained therein by a fastener member 175. Consequently, when the pivoting handle 22 is compressed in the direction of indicator arrow "B", elongated rod member 84 is pulled in a proximal direction (see FIG. 7), urging coupling member 88 to draw control cable 92 rearward so as to pull the engaging structure 40 into the V-shaped chamber 166 of passageway 160, camming engaging arms 182 and 184 into an engaging position. As engaging structure 40 extends into chamber 166, spring member 162 is compressed until such time as the T-shaped heads 186 and 188 of engaging arms 182 and 184 respectively, detachably engage surgical clamp 30.

Referring to FIGS. 3, 4 and 11–18, surgical clamp 30 includes an upper jaw member 32 and a lower jaw member 34 which are normally biased toward one another in a closed position. Upper jaw member 32 includes body portion 190 which has a tissue engaging surface 191 with a plurality of longitudinal striations 192 of triangular cross-section defined thereon, and a flange portion 193 having a pair of spaced apart apertures 194 and 195 extending therethrough for interconnection with lower jaw member 34. Lower jaw member 34 comprises an elongated body portion 196 which has a tissue engaging surface 197 having a plurality of elongated striations 198 of triangular cross-section defined thereon. Triangular striations 198 on the tissue engaging surface 197 of lower jaw member 34 may be adapted and configured for intermeshing with triangular striations 192 on the tissue engaging surface 191 of upper jaw member 32 when the opposed jaw members 32 and 34 are in a closed position. The body portion 196 of lower jaw member 34 depends from a base portion 199 and has a cross-section of generally circular configuration. A pivot aperture 204 is provided in flange portion 193 for receiving a pivot pin 206 which movably connects upper jaw member 32 to lower jaw member 34 through aperture 192 in the flange portion 193 of upper jaw member 32. A longitudinal groove 205 is provided in base portion 199 of lower jaw member 34 for accommodating the flange portion 193 of upper jaw member 32 and associated structure. Opposed lateral slots 208 and 210 are also defined in the base portion 198 of lower jaw member 34 for receiving engaging arms 182 and 184 of engaging structure 40 so as to detachably maintain surgical clamp 30 at the distal end of articulating portion 28. A bore hole 212 extends longitudinally into the base portion 199 of lower jaw member 34, from the proximal end thereof, for accommodating barrel member 36 and a spring 214 which biases barrel member 36 in a proximal direction.

Referring to FIGS. 3, 4, 17 and 18, barrel member 36 has a circular cross-section and is defined by an elongated body portion 220 and a rod portion 222. A traverse bore 224 extends through body portion 220 and a perpendicular slot 226 of rectangular configuration extends through body portion 220 for accommodating the movement of the flange portion 193 of upper jaw member 32 and a link member 230. Link member 230 is provided with a pair of spaced apart apertures 232 and 234. A pivot pin 236 extends through aperture 232 and the traverse bore 224 in barrel member 36 for operatively connecting the link member 230 to barrel member 36. Aperture 234 in link member 230 is provided for operatively receiving a rocker pin 235 which interconnect with aperture 195 in flange portion 193 of upper jaw member 32. When the opposed jaw members 32 and 34 of surgical clamp 30 are to be opened, manipulation of pivoting handle 22 will cause control cable 92 to draw the engaging structure 40 in a proximal direction, whereby surgical clamp 30 will move proximally relative to barrel member 36 in the direction of arrow "C" causing rocker pin 235 to urge upper jaw member 32 into an open position. During operations, the movement of upper jaw member 32 relative to lower jaw member 34 is unobstructed by barrel member 36 because the width "w" of the perpendicular slot 226 in the body portion 220 of barrel member 36 is approximately equal to the combined thickness of the flange portion 193 of upper jaw 32 and link member 230.

Figure 7:
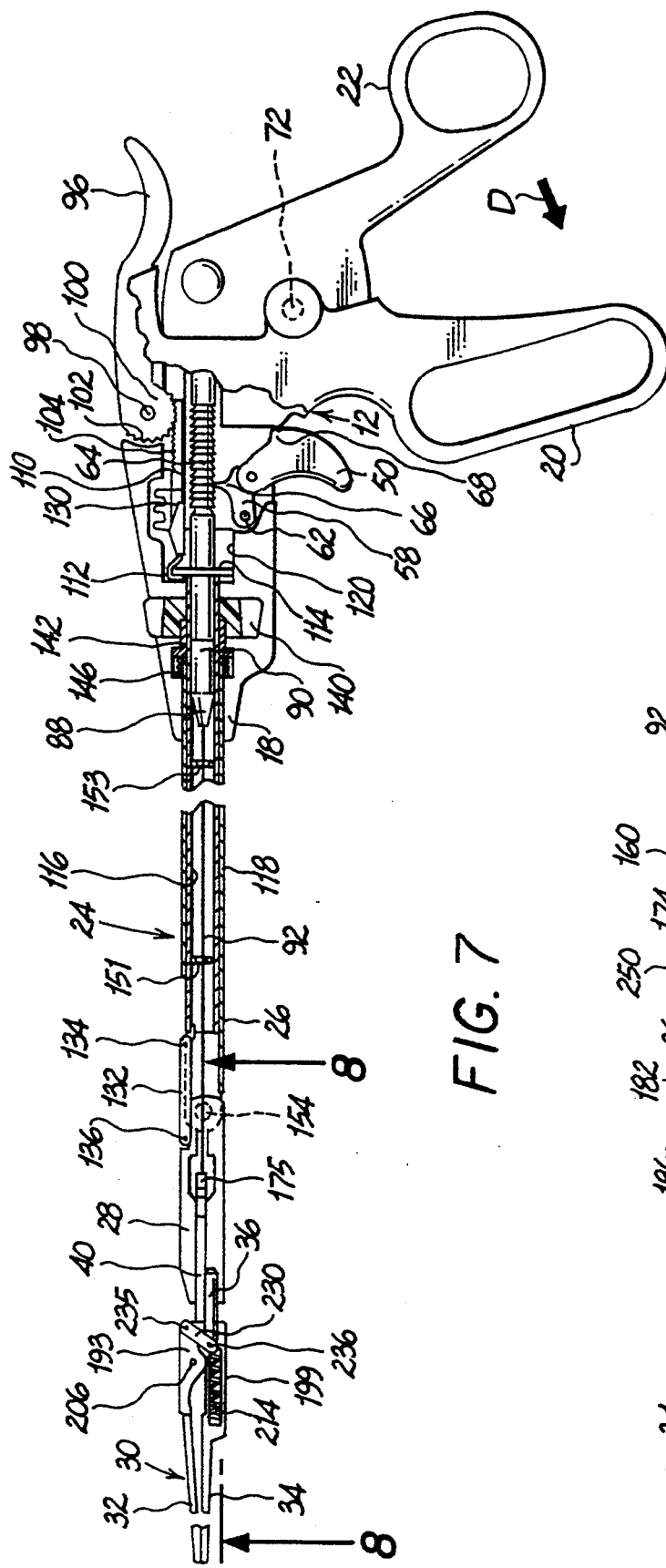
FIG. 7 is a side elevational view in cross-section of the apparatus of FIG. 1 with the pivoting handle in a partially closed position.
Figure 8:
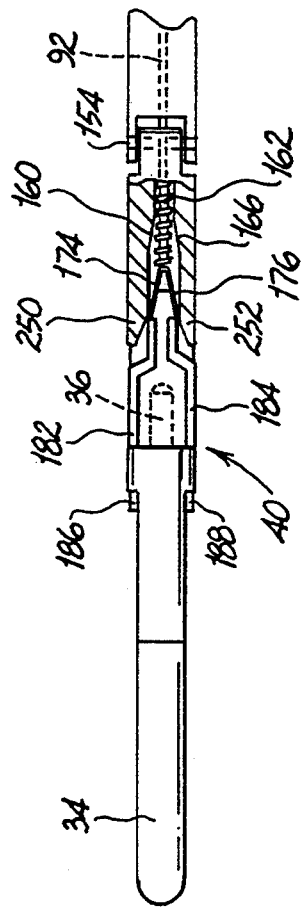
FIG. 8 is a top plan view in cross-section taken along line 8—8 of FIG. 7 with the engaging structure in an engaged position.

Referring to FIGS. 5-8, surgical apparatus 10 is prepared for introduction into a cannula device by detachably securing surgical clamp 30 adjacent the distal end of articulating portion 28. Securement of surgical clamp 30 is achieved by extending barrel member 36 into the distalmost chamber of passageway 160 in articulating portion 28. At such a time, the engaging arms 182 and 184 of engaging structure 40 extend radially outward from the longitudinal axis of the instrument and coiled spring 162 biases the engaging structure 40 distally as it exerts a force against the base 172 of resilient structural portion 170. Subsequently, as trigger 50 is compressed by the user so as to disengage catch 66 from the teeth in rack member 64, the pivoting handle 22 of handle portion 12 is compressed into an intermediate position in the direction of arrow "D", as illustrated in FIG. 7. Thereupon, rod member 84 is drawn in a proximal direction carrying with it rack member 64. Consequently, control cable 92 retreats within endoscopic portion 24 pulling engaging structure 40 into the V-shaped chamber 166 of passageway 160. As the engaging structure 40 is pulled into chamber 166, the opposed walls 250 and 252 thereof function to cam the engaging arms 182 and 184 into an engaged position where they are interlocked within the lateral slots 208 and 210 defined in the base portion 199 of the lower jaw member 34 of surgical clamp 30. At this time, the user releases trigger 50 so that catch 66 engages the teeth of rack member 64, thereby locking the control cable 92 in an intermediate position corresponding to the surgical clamp 30 being engaged at the distal end of the apparatus.

After clamp 30 has been detachably secured to articulating portion 28, the handle 22 may be pivoted in the direction indicated by arrow "D" to lock jaws 32 and 34 and then the endoscopic portion 24 of apparatus 10 may be introduced into the abdominal cavity of a patient through a cannula device. Thereafter, by rotating latch member 96 the user may articulate portion 28 to increase the range of operability of the instrument. In particular, referring to FIG. 9, rotation of latch member 96 in a counter-clockwise direction indicated by arrow "E", will translate rack member 104 in a proximal direction within longitudinal chamber 106. Thereupon, the hook structure 112 of draw arm 110 pulls the flange 114 of inner tube structure 116 rearwardly within the chamber 120 defined in barrel 18, causing inner tube structure 116 to travel in a proximal direction within the outer tube 118 of endoscopic portion 24. Consequently, articulating link 132 is urged in a generally proximal direction causing the articulating portion 28 to rotate in a clock-wise direction indicated by arrow "F" about transverse pivot pin 154. The degree of angular rotation of articulating portion 28 can be selected by moving the leaf spring 126 relative to groove structure 130 so that engaging detent 128 is received within one of the grooved areas provided therein.

Figure 9:
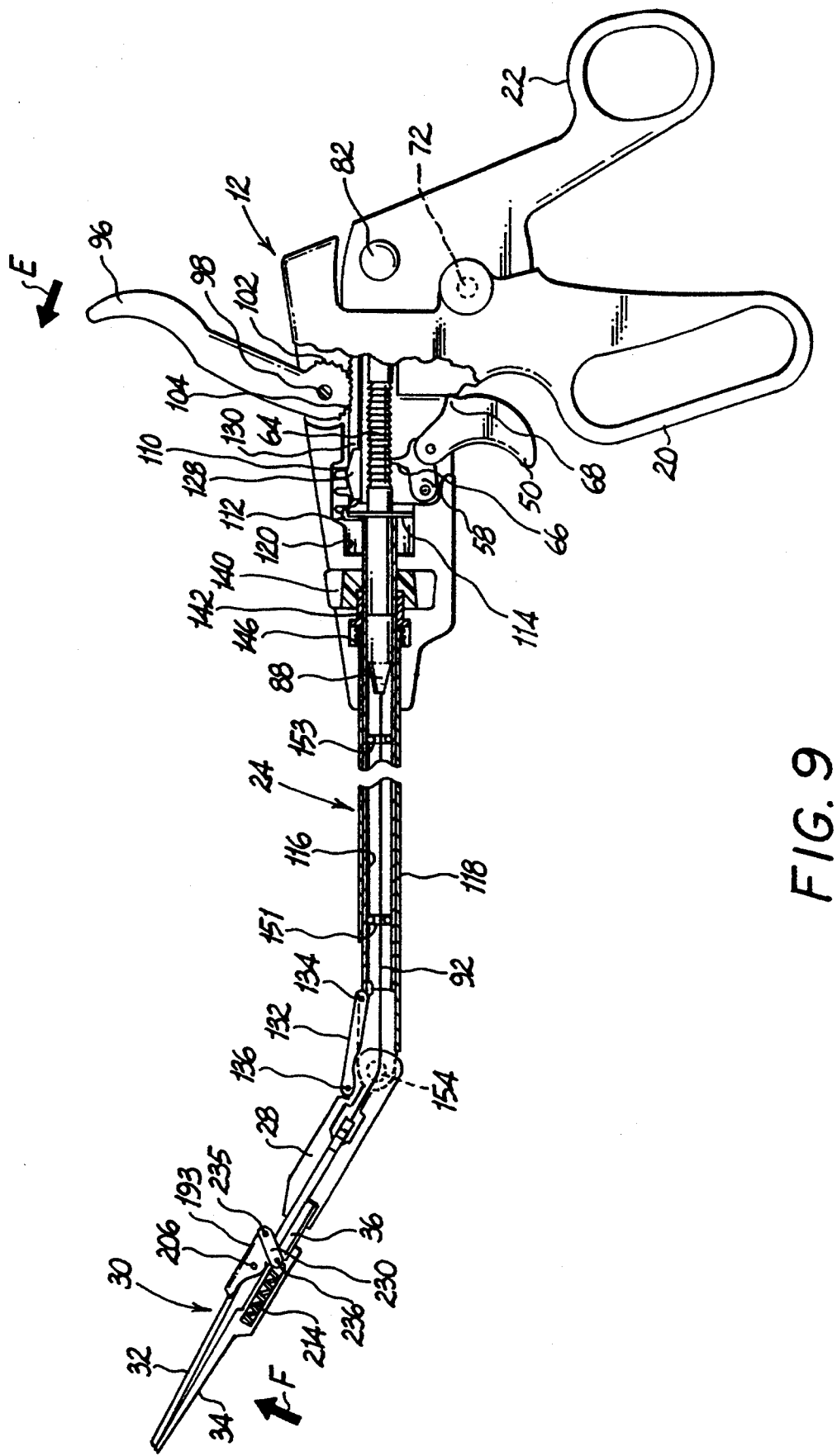
FIG. 9 is a side elevational view in cross-section of the apparatus of FIG. 1, with the distal end portion thereof in an articulated position.
Figure 10:
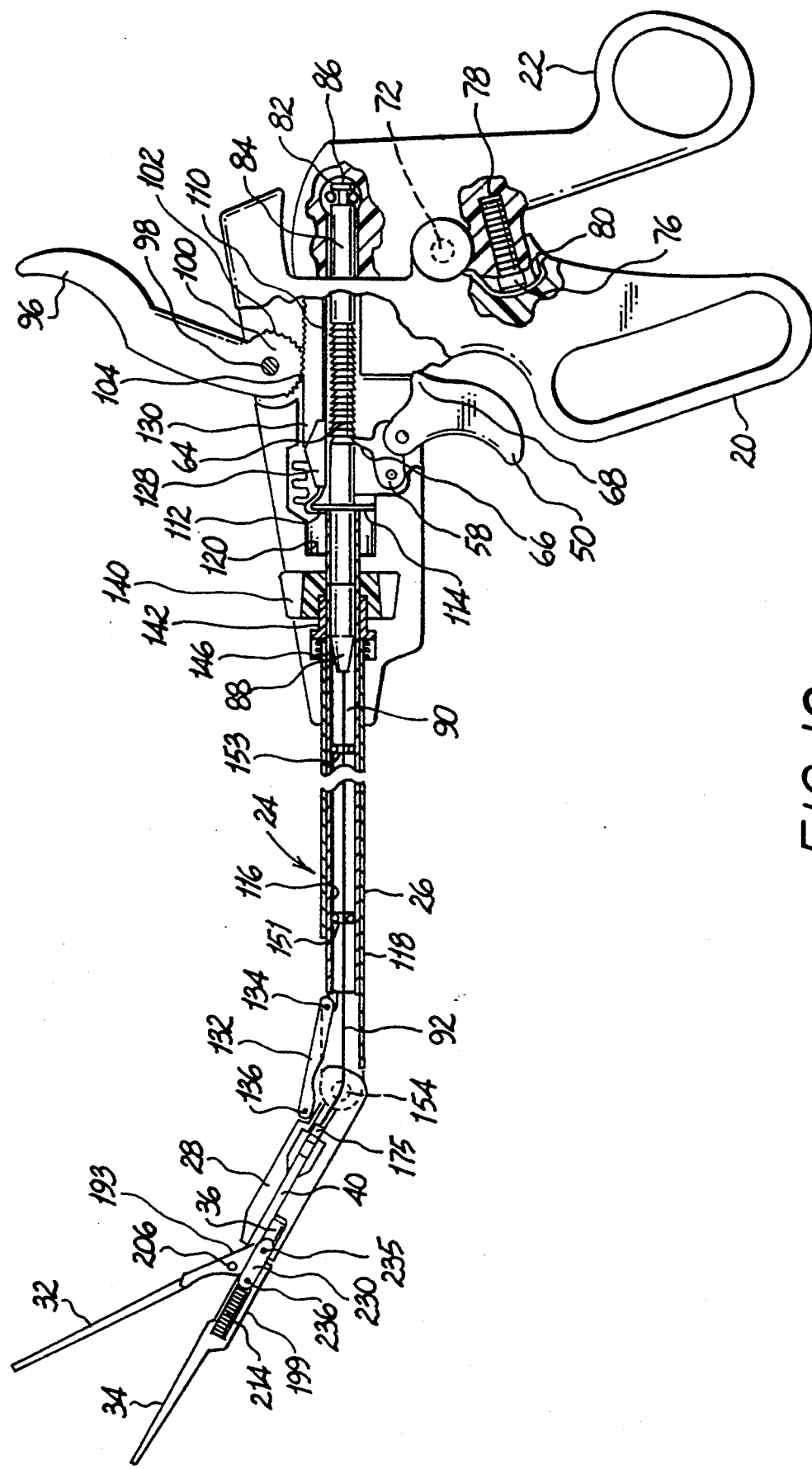
FIG. 10 is a side elevational view in cross-section of the apparatus of FIG. 1, with the distal end portion thereof in an articulated position wherein the clamp is in an open position.

When apparatus 10 is in a desired articulated position, the user may move the cooperating jaw members 32 and 34 of surgical clamp 30 from the initially closed position of FIG. 9, to the open position of FIG. 10, by compressing pivoting handle 22 into a fully compressed position. First, the user depresses trigger 50 so as to release catch 66 from the teeth of rack member 64. Then, pivoting handle 22 is fully compressed so as to draw the head portion 86 of rod member 84 to its proximal-most position. At such a time, coupling member 88 moves proximally within endoscopic portion 24, drawing control cable 92 in a proximal direction, and thereby pulling engaging structure 40 further into passageway 160 in articulating portion 28. Thereupon, surgical clamp 30 is drawn in a generally proximal direction as spring member 214 is compressed against barrel member 36 within the bore hole 212 defined in lower jaw 34. Consequently, link member 230 translates relative to the base portion 198 of lower jaw 34 causing the upper jaw member 32 to be moved into a open position.

Once jaw members 32 and 34 have been moved into an open position, surgical clamp 30 may be placed in a desired location on the intestine adjacent the area to be opened. Surgical clamp 30 may be easily repositioned by depressing trigger 50 while maintaining pivoting handle 22 in the intermediate position of FIG. 9. This may be repeated until clamp 30 has been properly positioned on the intestine. When the clamp 30 has been properly positioned, the user of the instrument can depress trigger 50 so as to once again release rack member 64. Thereupon, pivoting handle 22 returns to its decompressed position under the influence of biasing spring 74. As pivoting handle 22 moves, rod member 84 is urged in a distal direction permitting control cable 92 to advance distally within endoscopic portion 24. At such a time, the spring 162 in passageway 160 urges engaging structure 40 forward causing the opposed engaging arms 182 and 184 to disengage from lateral slots 208 and 210, thereby detaching the surgical clamp 30 from the endoscopic portion 24 of apparatus 10. Once surgical clamp 30 has been detached, the articulating portion 28 may be manipulated to its longitudinally aligned position and the instrument may be withdrawn from the cannula device.

When the surgical procedure has been completed, the endoscopic portion of the apparatus may be once again extended through the cannula device and into the abdominal cavity of the patient to retrieve the surgical clamp. Retrieval of surgical clamp 30 is achieved by manipulating the engaging structure 40 to engage clamp 30 so that it may be moved to an open position and removed from the intestine.

It is envisioned that the present invention would be marketed in a wide variety of configurations including the apparatus in conjunction with a plurality of clamp assemblies either of the same or varying sizes such as for example at least one 30 mm clamp, and/or at least one 45 mm clamp, and/or at least one 60 mm clamp. Further, the invention could be presented with an assortment of other surgical instrumentation which would be utilized in the course of a particular procedure. These instruments could include surgical fastening apparatus and/or clip appliers, trocars, cannulae, grippers, dissectors, forceps, insufflation needles, etc.

Although the endoscopic surgical apparatus of the subject invention has been described with respect to a preferred embodiment, it is apparent that modifications or changes may be made to the instrument without departing from the spirit or scope of the invention as described by the appended claims.

What is claimed is:

1. Apparatus for applying and retrieving a surgical clamp comprising:
   a) a handle portion;
   b) an endoscopic portion having a proximal end and a distal end, said proximal end extending longitudinally from said handle portion;
   c) a surgical clamp detachably mounted adjacent said distal end of said endoscopic portion and including opposed cooperating jaw members remotely actuable to move in a first plane between a first position and a second position by actuation means controllable from said handle portion; and
   d) engaging means associated with said distal end of said endoscopic portion for detachably engaging and retrieving said surgical clamp, said engaging means including opposed engaging arm members movable in a second plane between a primary position in engagement with said surgical clamp and a secondary position spaced from said surgical clamp to facilitate detachment of said surgical clamp from said endoscopic portion, said arm members actuable remote from said distal end of said endoscopic portion and movable in a longitudinal direction relative to the endoscopic portion to effect movement of said cooperating jaw members in said first plane.

2. Apparatus as recited in claim 1, wherein a distal portion of said endoscopic portion is movably connected to a proximal portion of said endoscopic portion.

3. Apparatus as recited in claim 2, further comprising means associated with said handle portion for effectuating the articulation of said distal portion of said endoscopic portion relative to a longitudinal axis of said proximal portion.

4. Apparatus as recited in claim 3, wherein said means for effectuating the articulation of said distal portion comprises a rack member mounted for reciprocating longitudinal movement in said handle portion in response to rotation of a pinion member.

5. Apparatus as recited in claim 1, wherein said first position corresponds to said opposed cooperating jaw members being in an open position.

6. Apparatus as recited in claim 1, wherein said surgical clamp includes means for biasing said opposed cooperating jaw members in said second position corresponding to said jaw members being in a closed position.

7. Apparatus as recited in claim 6, wherein said surgical clamp includes an upper jaw member and a lower jaw member, said lower jaw member having a cavity defined therein for accommodating said biasing means and at least a portion of a barrel member biased by said biasing means, said upper jaw member being operatively connected to said barrel member for biasing said upper jaw member toward said lower jaw member.

8. Apparatus as recited in claim 7, wherein said opposed cooperating jaw members include link means for guiding the cooperative movement of said opposed jaw members between said first position and said second position.

9. Apparatus as recited in claim 8, wherein said link means comprises a pivoting link member connecting said upper jaw member to said barrel member to effect relative movement of said opposed jaw members.

10. Apparatus as recited in claim 1, wherein each of said opposed engaging arm members have a generally T-shaped head portion which detachably engage corresponding slots formed in said surgical clamp.

11. Apparatus as recited in claim 1, wherein said engaging means includes an extension member operatively associated with a pivoting handle of said handle portion and extending through said endoscopic portion to said detachable engaging means.

12. Apparatus as recited in claim 11, wherein a ratcheting mechanism is associated with said extension member and is actuable independent of said pivoting handle for selectively maintaining said extension member in a desired longitudinal position.

13. Apparatus as recited in claim 13, wherein said ratcheting mechanism selectively maintains said extension member in a first longitudinal position corresponding to said opposed engaging arm members moving into an engaged position and a second longitudinal position corresponding to said opposed jaw members moving into an open position.

14. Apparatus as recited in claim 1, further comprising seal means associated with said endoscopic portion for inhibiting the egress of insufflation gas therethrough.

15. Apparatus for applying and retrieving a surgical clamp comprising:
   a) a handle portion;
   b) an endoscopic portion including a proximal portion extending longitudinally from said handle portion and a distal portion connected to said proximal portion;
   c) a surgical clamp detachably mounted adjacent a distal end of said distal portion, said surgical clamp including opposed cooperating jaw members initially biased in a first position and remotely movable in a first plane to a second position;
   d) engaging means associated with said distal portion of said endoscopic portion for detachably engaging and retrieving said surgical clamp, said engaging means including opposed engaging arm members movable in a second plane between a primary position in engagement with said surgical clamp and a secondary position spaced from said surgical clamp to facilitate detachment of said surgical clamp from said endoscopic portion, said arm members actuable remote from said distal end of said endoscopic portion and movable in a longitudinal direction relative to the endoscopic portion to effect movement of said cooperating jaw members in said first plane; and
   e) means associated with said handle portion for articulating said distal portion of said endoscopic portion relative to a longitudinal axis of said proximal portion.

16. Apparatus as recited in claim 15, wherein said means for articulating said distal portion comprises a rack member mounted for reciprocating longitudinal movement in said handle portion in response to rotation of a pinion member.

17. Apparatus as recited in claim 16, wherein said surgical clamp includes an upper jaw member and a lower jaw member, said lower jaw member having a cavity defined therein for accommodating biasing means and at least a portion of a barrel member biased by said biasing means, said upper jaw member being operatively connected to said barrel member for biasing said upper jaw member toward said lower jaw member.

18. Apparatus as recited in claim 17, wherein a link member connects said upper jaw member to said barrel member for directing the movement of said opposed jaw members between said first position and said second position.

19. Apparatus as recited in claim 15, wherein each of said opposed engaging arm members have a generally T-shaped head portion which engage corresponding slots formed in said surgical clamp.

20. Apparatus as recited in claim 15, wherein an extension member operatively associated with a pivoting handle in said handle portion extends through said endoscopic portion to said opposed engaging arm members for moving said arm members between said primary position and said secondary position.

21. Apparatus as recited in claim 20, wherein a ratcheting mechanism is associated with said extension member and is actuable independent of said pivoting member for selectively maintaining said extension member in a desired longitudinal position.

22. Apparatus as recited in claim 21, wherein said ratcheting mechanism is provided to selectively maintain said extension member in a first longitudinal position corresponding to said opposed engaging arm members being moved into an engaged position and a second longitudinal position corresponding to said opposed jaw members being moved into an open position.

23. Apparatus as recited in claim 15, wherein said first plane is orthogonal to said second plane.

24. Apparatus for applying and retrieving a surgical clamp comprising:
   a) a handle portion;
   b) an endoscopic portion including a proximal portion extending longitudinally from said handle portion and a distal portion movably connected to said proximal portion;
   c) means for articulating said distal portion of said endoscopic portion relative to a longitudinal axis of said proximal portion;
   d) a surgical clamp detachably mounted adjacent a distal end of said distal portion, said surgical clamp including opposed cooperating jaw members initially biased in a first position and remotely actuable to move to a second position;
   e) a pair of opposed engaging arm members for detachably engaging and retrieving said surgical clamp, said opposed engaging arm members each having a camming surface associated therewith, said arm members actuable remote from said distal end of said endoscopic portion; and
   f) actuation structure associated with said handle portion for camming said engaging arm members between a primary position wherein said engaging arm members are in engagement with said surgical clamp and a secondary position wherein said engaging arm members are spaced from said surgical clamp, and for moving said cooperating jaw members between said first position and said second position by translating in a longitudinal direction relative to the endoscopic portion.

25. Apparatus as recited in claim 24, wherein said means for articulating said distal portion comprises a rack member mounted for reciprocating longitudinal movement in said handle portion in response to rotation of a pinion member.

26. Apparatus as recited in claim 24, wherein said surgical clamp includes an upper jaw member and a lower jaw member, said lower jaw member having a cavity defined therein for accommodating biasing means and at least a portion of a barrel member, said upper jaw member being operatively connected to said barrel member for biasing said upper jaw member in said closed position.

27. Apparatus as recited in claim 24, wherein each of said opposed engaging arm members have a generally T-shaped head portion which engage corresponding slots formed in said surgical clamp.

28. Apparatus as recited in claim 24, wherein said actuation structure for moving said cooperating jaw members comprises an extension member operatively associated with a pivoting handle in said handle portion and extending through said endoscopic portion to said opposed engaging arm member.

29. Apparatus as recited in claim 28, wherein a ratcheting mechanism is associated with said extension member and is actuable independent of said pivoting handle for selectively maintaining said extension member in a desired longitudinal position.

30. Apparatus as recited in claim 29, wherein said ratcheting mechanism is provided for selectively maintaining said extension member in a first longitudinal position corresponding to said opposed engaging arm members being cammed into an engaged position and a second longitudinal position corresponding to said opposed jaw members being moved into an open position.

31. Apparatus as recited in claim 24, further comprising seal means associated with said endoscopic portion for inhibiting the egress of insufflation gas therethrough.

32. An apparatus for applying a surgical clamp to body tissue comprising:
   a) a handle assembly including a pivoting actuation handle;
   b) an elongated body extending distally from the handle assembly and defining a longitudinal axis;
   c) a pair of cooperating actuation arms operatively associated with a distal end of the elongated body;
   d) a surgical clamp detachably supported at the distal end of the elongated body and including a pair of cooperating jaws movable in a first plane between open and closed positions; and
   e) an actuator extending from the actuation handle to the actuation arms to translate motion therebetween, wherein movement of the actuation handle through a first distance effects movement of the actuation arms in a second plane between a first position spaced from the surgical clamp and a second position engaged with the surgical clamp, and movement of the actuation handle through a second distance effects longitudinal translation of the actuation arms relative to the elongated portion while in the second position to effect movement of the cooperating jaws in the first plane.

* * * * *